United States Patent
Ohki et al.

(10) Patent No.: US 8,180,437 B2
(45) Date of Patent: May 15, 2012

(54) OPTICAL PULSE WAVE VELOCITY OBTAINING APPARATUS AND METHOD THEREOF

(75) Inventors: Mitsuharu Ohki, Tokyo (JP); Tomonori Masuno, Tokyo (JP)

(73) Assignee: Sony Corporation, Tokyo (JP)

( * ) Notice: Subject to any disclaimer, the term of this patent is extended or adjusted under 35 U.S.C. 154(b) by 955 days.

(21) Appl. No.: 12/131,640

(22) Filed: Jun. 2, 2008

(65) Prior Publication Data

US 2008/0306372 A1    Dec. 11, 2008

(30) Foreign Application Priority Data

Jun. 6, 2007    (JP) .................................. 2007-149858

(51) Int. Cl.
*A61B 6/00*    (2006.01)
(52) U.S. Cl. .................... 600/479; 600/500; 600/504
(58) Field of Classification Search .................. 600/323, 600/324, 473, 500, 504, 407, 475–482, 485
See application file for complete search history.

(56) References Cited

U.S. PATENT DOCUMENTS

| | | | |
|---|---|---|---|
| 6,758,819 B2 | 7/2004 | Nomura | |
| 2003/0069485 A1 | 4/2003 | Konishi et al. | |
| 2007/0016085 A1 | 1/2007 | Inukai et al. | |
| 2009/0118623 A1 * | 5/2009 | Serov et al. | 600/476 |

FOREIGN PATENT DOCUMENTS

| | | |
|---|---|---|
| EP | 1 344 488 A2 | 9/2003 |
| JP | 2003-230543 | 8/2003 |
| WO | WO 2006/100685 A2 | 9/2006 |
| WO | WO 2006/111836 A1 | 10/2006 |

OTHER PUBLICATIONS

U.S. Appl. No. 12/110,537, filed Apr. 28, 2008, Ohki, et al.

* cited by examiner

*Primary Examiner* — Ruth S Smith
(74) *Attorney, Agent, or Firm* — Oblon, Spivak, McClelland, Maier & Neustadt, L.L.P.

(57) ABSTRACT

A biological-information obtaining apparatus includes a light-emitting unit, an image sensor configured to capture images, in a time sequence, relating to a living body, and a lens. The apparatus also includes an extreme-occurrence-time obtaining unit configured to obtain times T1 and T2 at which extremes occur in time sequence with respect to brightness values of a first region and a second region, respectively, of each of the captured images. The apparatus further includes a pulse wave velocity (PWV) calculation unit configured to calculate a pulse wave velocity according to the equation, $P=(Y \times L/f)/(T2-T1)$, where Y represents a distance on the image sensor, the distance corresponding to a distance between the first region and the second region, f represents the focal length of the lens, and L represents a distance between the lens and the living body.

8 Claims, 6 Drawing Sheets

OPTICAL PULSE WAVE VELOCITY OBTAINING APPARATUS AND METHOD THEREOF

CROSS REFERENCES TO RELATED APPLICATIONS

The present invention contains subject matter related to Japanese Patent Application JP 2007-149858 filed in the Japanese Patent Office on Jun. 6, 2007, the entire contents of which are incorporated herein by reference.

BACKGROUND OF THE INVENTION

1. Field of the Invention

The present invention relates to a biological-information obtaining apparatus, particularly to a biological-information obtaining apparatus capable of obtaining a pulse wave velocity (PWV) and a processing method thereof.

2. Description of the Related Art

The PWV represents the propagation velocity of a pulse wave propagating through arteries, and is known for its helpfulness in finding cardiovascular diseases such as arterial sclerosis. As a method of determining such a PWV, for example, use of an apparatus is known that determines two locations used in the detection of a cardiac-beat synchronizing signal in blood-vessel patterns and determines a PWV on the basis of the distance between the two locations and the time when the cardiac-beat synchronizing signal is generated.

As such an apparatus, for example, an apparatus with a phonocardiographic transducer to be attached onto the skin of the chest and a pressure sensor to be wound around the brachial region has been developed for determining a PWV. Regarding such an apparatus with a phonocardiographic transducer and pressure sensor, a method of determining the length of a blood vessel has been proposed (see, for example, Japanese Unexamined Patent Application Publication No. 2003-230543, FIG. 1). In this example of the related art, the speed at which an ultrasonic wave propagates in biomedical tissue is stored, and the length of the blood vessel is calculated by dividing an observed value of the ultrasonic wave output from the phonocardiographic transducer by the speed.

SUMMARY OF THE INVENTION

In the above-described example of the related art, the pulse wave propagation time is determined using the phonocardiographic transducer and pressure sensor so that the PWV is obtained. However, a large-scale determining apparatus is necessary in order to determine such a pulse wave propagation time over the entire body. Thus, it may be inappropriate for daily determination.

It is desirable to downsize a biological-information obtaining apparatus used for obtaining a PWV.

According to an embodiment of the present invention, there is provided a biological-information obtaining apparatus including light-emitting means for emitting light, an image sensor for capturing images, in time sequence, obtained by irradiating a living body with the light emitted and by causing the light to be transmitted through or reflected by the living body, a lens for causing the images to be formed on the image sensor, extreme-occurrence-time obtaining means for obtaining times T1 and T2 at which extremes occur in time sequence with respect to brightness values of a first region and a second region of each of the captured images, the time T1 being obtained for one of the first regions and the time T2 being obtained for one of the second regions, and pulse-wave-velocity calculation means for calculating a pulse wave velocity $P=(Y \times L/f)/(T2-T1)$, where Y represents a distance on the image sensor, the distance corresponding to a distance between the first region and the second region, f represents the focal length of the lens, and L represents a distance between the lens and the living body in the case of capturing the images. This allows calculation of a PWV on the basis of changes in time sequence with respect to brightness of the captured images.

In the biological-information obtaining apparatus, the light-emitting means may emit monochromatic light from a monochromatic light source. Alternatively or additionally, an incandescent lamp, a halogen lamp, a white light-emitting diode, or a red light-emitting diode may be used.

In the biological-information obtaining apparatus, the extreme-occurrence-time obtaining means may obtain the times T1 and T2 at which the extremes occur in time sequence with respect to brightness averages of the first region and the second region of each of the captured images, the time T1 being obtained for one of the first regions and the time T2 being obtained for one of the second regions. This allows absorbance of an effect caused by a local change.

In the biological-information obtaining apparatus, the extreme-occurrence-time obtaining means may obtain the times T1 and T2 at which the extremes occur in time sequence with respect to brightness averages of the first region and the second region of each of the captured images, the first region and the second region being obtained by halving the captured image, the time T1 being obtained for one of the first regions and the time T2 being obtained for one of the second regions, and the pulse-wave-velocity calculation means may calculate the pulse wave velocity $P=(Y \times L/f)/(T2-T1)$, where Y representing a distance on the image sensor, the distance corresponding to a distance between midpoints of the first and ant-second regions. This allows calculation of a PWV by using the first and second regions, as the basis, obtained by halving the captured image.

According to another embodiment of the present invention, there is provided a biological-information obtaining apparatus including light-emitting means for emitting light, an image sensor for capturing images, in time sequence, obtained by irradiating a living body with the light emitted and by causing the light to be transmitted through or reflected by the living body, a lens for causing the images to be formed on the image sensor, parameter storing means for storing, as parameters, a length K of the image sensor, the focal length f of the lens, and a distance L between the lens and the living body in the case of capturing the images, extreme-occurrence-time obtaining means for obtaining times T1 and T2 at which extremes occur in time sequence with respect to brightness averages of a first region and a second region of each of the captured images, the first region and the second region being obtained by halving the captured image, the time T1 being obtained for one of the first regions and the time T2 being obtained for one of the second regions, and pulse-wave-velocity calculation means for calculating a pulse wave velocity $P=((K/2) \times L/f)/(T2-T1)$ on the basis of the times T1 and T2 obtained by the extreme-occurrence-time obtaining means and the parameters stored in the parameter storing means. This allows calculation of a PWV on the basis of specific parameters and changes in time sequence with respect to brightness of the captured image.

According to the embodiments of the present invention, the biological-information obtaining apparatus used for obtaining the PWV can be downsized.

DESCRIPTION OF THE PREFERRED EMBODIMENTS

Embodiments of the present invention will be described in detail with reference to the attached drawings.

Figure 1:
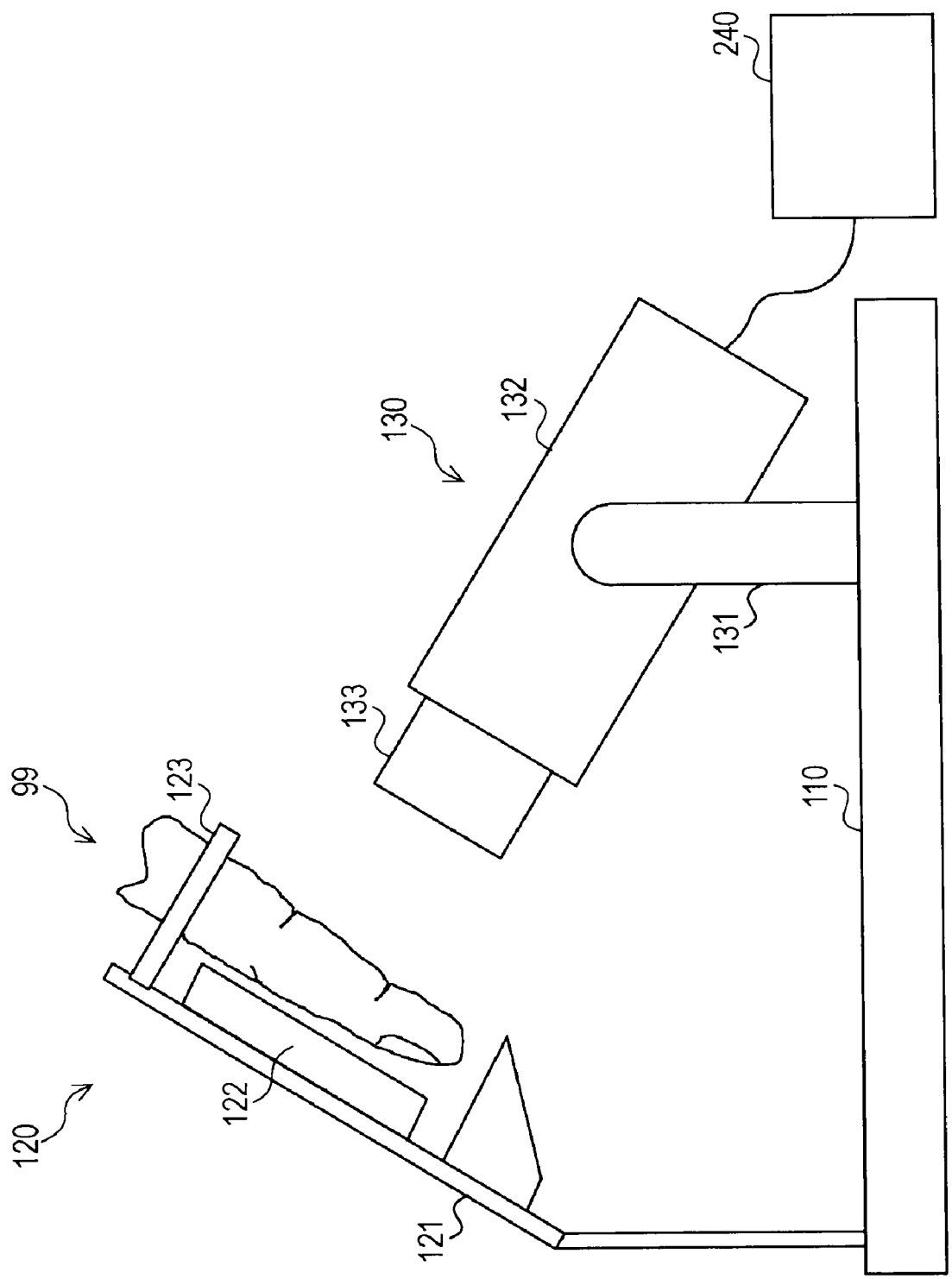
FIG. 1 is a diagram showing an exemplary side view of a biological-information obtaining apparatus according to an embodiment of the present invention.

FIG. 1 is a diagram showing an exemplary side view of a biological-information obtaining apparatus according to an embodiment of the present invention. In this biological-information obtaining apparatus, an irradiation unit 120 and an image-capturing unit 130 are provided on a base 110.

The irradiation unit 120 includes a support portion 121, a light-emitting portion 122, and an insertion opening 123. The support portion 121 has one end thereof connected to the base 110 in order to support the entirety of the irradiation unit 120. The light-emitting portion 122 emits light with which a part of a living body is irradiated. According to the embodiment of the present invention, the color of the light is not particularly specified. For example, an incandescent lamp, a halogen lamp, a monochromatic light source, a white light-emitting diode or a red light-emitting diode may be used. The insertion opening 123 is a leading opening through which, for example, a finger 99 is inserted as a part of the living body.

For the light-emitting portion 122, the number of, for example, incandescent lamps or the rated power may be appropriately selected. Solar rays may be used as a light source instead of, for example, incandescent lamps when the entirety of the biological-information obtaining apparatus is exposed to the sun and the finger 99 is placed therebetween.

The image-capturing unit 130 includes a support portion 131 and a camera body 132. The support portion 131 has one end thereof connected to the base 110 and supports the camera body 132. The camera body 132 is used to capture an image of a subject, and may be a general digital still camera or digital video camera or a dedicated camera. It is desirable that the camera body 132 have a continuous shooting mode for shooting a plurality of images in sequence.

A lens unit 133 is provided at a front end of the camera body 132, and is fixed and held by the support portion 131 such that the shooting axis of the lens unit 133 becomes orthogonal to the light-emitting portion 122. The camera body 132 converts the light collected by the lens unit 133 into an electric signal by using an image pickup device. Such an image pickup device may be a one-dimensional line sensor or a two-dimensional image sensor, and can be realized by using a charge-coupled device (CCD) sensor or a complementary metal oxide semiconductor (CMOS) sensor. As the image pickup device, one of image pickup devices sensitive to three colors of red (R), green (G), and blue (B) may often be used.

In this case, such an image pickup device is usually sensitive to wavelengths from about 800 nm through about 1000 nm. That is, near infrared rays are also receivable.

Images captured by the camera body 132 are sequentially transferred to an image-processing unit 240. The image-processing unit 240 may be achieved using dedicated hardware or a general personal computer.

Figure 2:
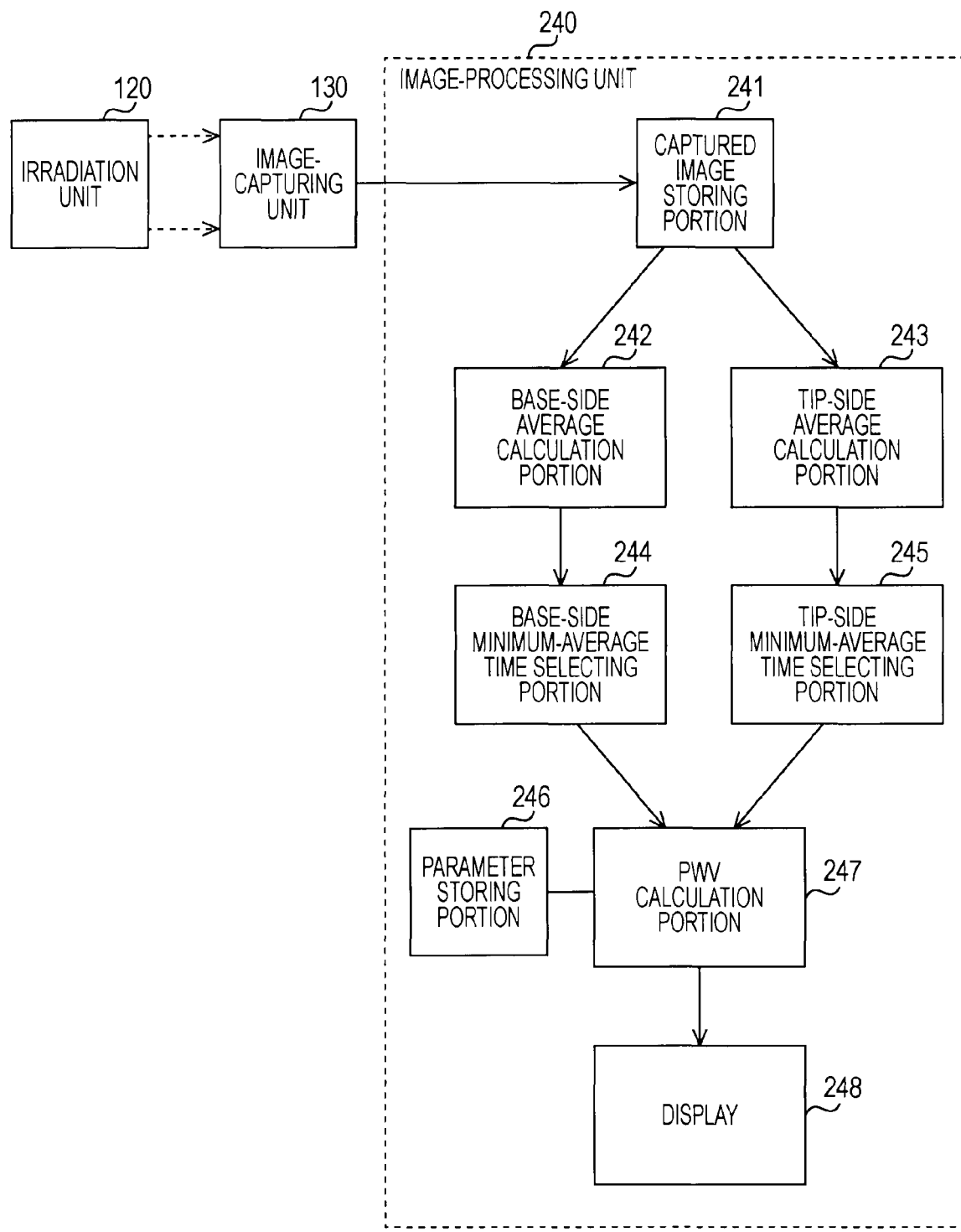
FIG. 2 is a functional block diagram showing an image-processing unit according to the embodiment of the present invention.

FIG. 2 is a functional block diagram showing the image-processing unit 240 according to the embodiment of the present invention. The image-processing unit 240 receives images supplied from the image-capturing unit 130, the images being obtained by irradiating the part of the living body with light emitted by the irradiation unit 120 and by causing the light to be transmitted through the living body. The image-processing unit 240 includes a captured image storing portion 241, a base-side average calculation portion 242, a tip-side average calculation portion 243, a base-side minimum-average time selecting portion 244, a tip-side minimum-average time selecting portion 245, a parameter storing portion 246, a PWV calculation portion 247, and a display 248.

The captured image storing portion 241 stores the images supplied from the image-capturing unit 130. The images are captured in time sequence. Here, it is assumed that the number of images is three hundred, corresponding to the number of images captured in five seconds at intervals of sixty images per second. Shorter intervals could provide a PWV with a higher degree of calculation accuracy; however, for practical purposes, the intervals are considered sufficiently short if the period is sufficiently shorter than a pulse (wave) cycle. In general, the pulse cycle is approximately 0.5 to 1 second, and thus if the intervals are shorter than 0.02 seconds (that is more than fifty images per second), the intervals are sufficiently short. Moreover, it is basically necessary that the overall shooting time period be almost the same as the pulse (wave) cycle; however, in order to perform stable determination, it is desirable that a period of approximately a few seconds be maintained for the overall shooting time period.

The base-side average calculation portion 242 calculates brightness averages of image portions concerning the base (root) portion of the finger 99. Each of the brightness averages is calculated with respect to a corresponding one of the images stored in the captured image storing portion 241. If time is represented by t (t is an integer), the brightness averages of the image portions concerning the base portion of the finger 99 are expressed by $AV1(t)$ in time sequence. Here, a brightness average in this case may be the average of the brightness of the entirety of an image portion concerning the base portion; however, if the base portion of the finger 99 does not appear in the peripheral area of the image portion, a brightness average of a central region (100×100 pixels around a midpoint) of the image portion concerning the base portion of the finger 99 may be calculated. In addition, a representative point such as the midpoint in the image portion concerning the base portion of the finger 99 may be used instead of the calculation of the brightness average in order to omit the average calculation process.

The tip-side average calculation portion 243 calculates brightness averages of image portions concerning the tip portion of the finger 99. Each of the brightness averages is calculated with respect to a corresponding one of the images stored in the captured image storing portion 241. Similarly to the case of the base portion, if time is represented by t, the brightness averages of the image portions concerning the tip portion of the finger 99 are expressed by $AV2(t)$ in time sequence. Here, the brightness averages are calculated similarly to the case of the base portion.

The base-side minimum-average time selecting portion 244 selects a time when it is determined that a minimum brightness average occurs in time sequence among the brightness averages $AV1(t)$ of the image portions concerning the base portion of the finger 99, the brightness averages $AV1(t)$ being calculated by the base-side average calculation portion 242.

The tip-side minimum-average time selecting portion 245 selects a time when it is determined that a minimum brightness average occurs in time sequence among the brightness averages $AV2(t)$ of the image portions concerning the tip portion of the finger 99, the brightness averages $AV2(t)$ being calculated by the base-side average calculation portion 243.

The parameter storing portion 246 stores known parameters necessary for the calculation of a PWV. Such parameters will be described in detail below.

The PWV calculation portion 247 calculates a PWV on the basis of the time selected by the base-side minimum-average time selecting portion 244, the time selected by the tip-side minimum-average time selecting portion 245, and the parameters held by the parameter storing portion 246. A method of calculating a PWV performed by the PWV calculation portion 247 will be described below.

The display 248 displays the PWV calculated by the PWV calculation portion 247. The display 248 may be achieved using, for example, a liquid crystal display (LCD) panel.

Figure 3:
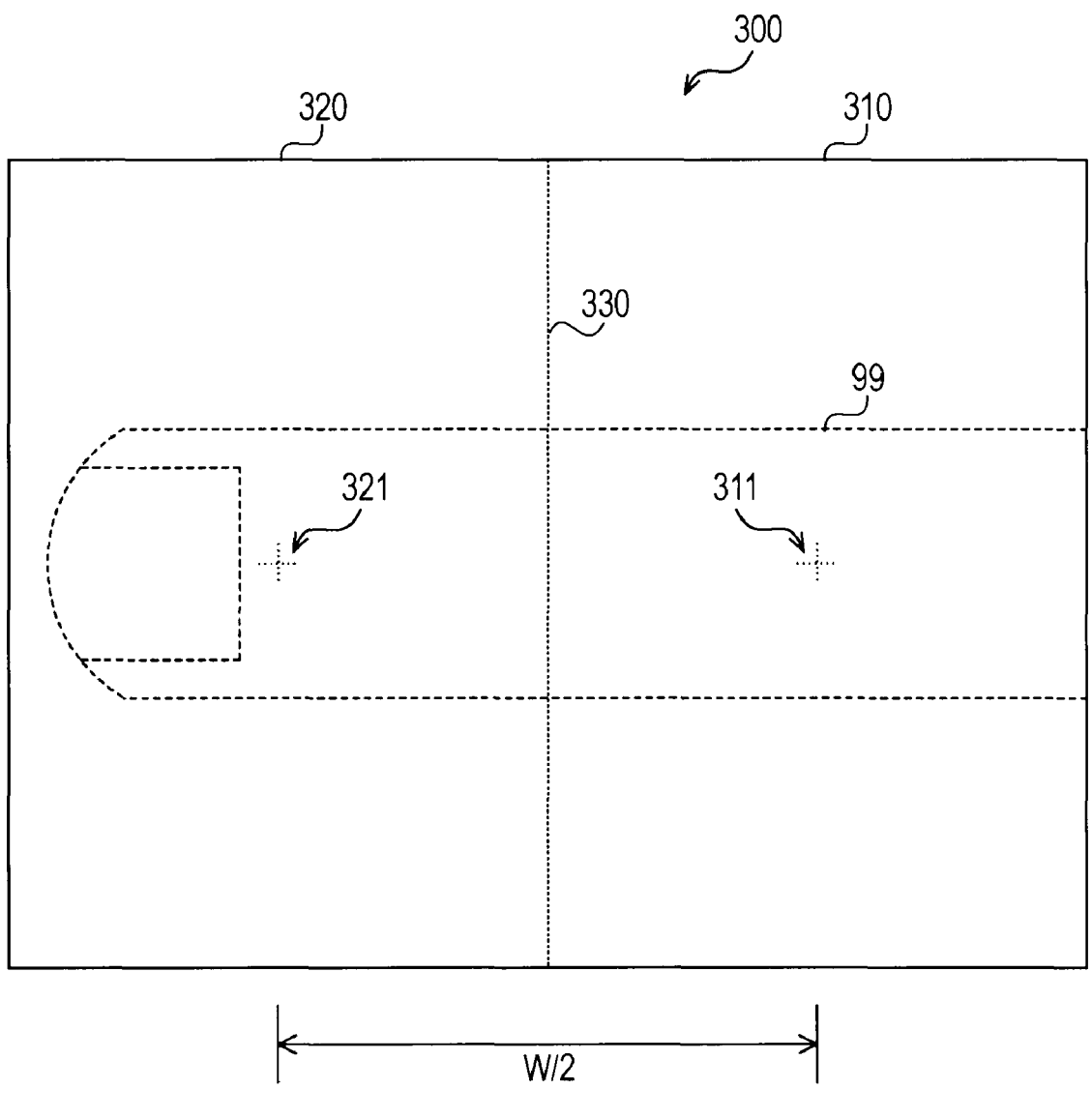
FIG. 3 is a diagram showing an example of a captured image according to the embodiment of the present invention.

FIG. 3 is a diagram showing an example of a captured image 300 according to the embodiment of the present invention. Here, the captured image 300 is divided into two regions by a center line 330, and a brightness of each of the two regions is determined. In FIG. 3, the right region represents a base-side image portion 310 of the finger 99, and the left region represents a tip-side image portion 320 of the finger 99. The base-side average calculation portion 242 calculates a brightness average of the base-side image portion 310, and the tip-side average calculation portion 243 calculates a brightness average of the tip-side image portion 320.

Here, a midpoint 311 of the base-side image portion 310 is assigned as a representative point of the base-side image portion 310, and a midpoint 321 of the tip-side image portion 320 is assigned as a representative point of the tip-side image portion 320. Here, if the horizontal length of the captured image 300 is W, the distance between the midpoint 311 of the base-side image portion 310 and the midpoint 321 of the tip-side image portion 320 is W/2, which is half the horizontal length of the captured image 300.

Figure 4A:
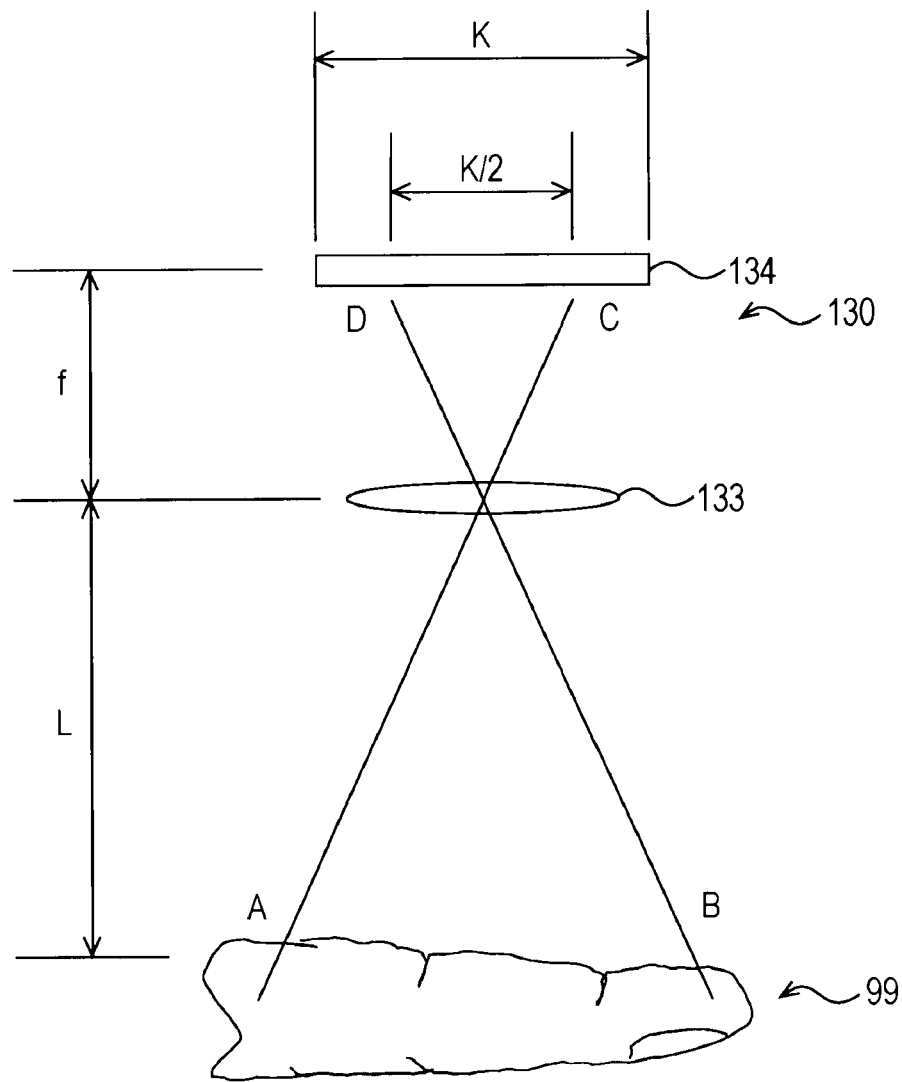
FIGS. 4A and 4B are diagrams showing a positional relation between an image-capturing unit and a finger according to the embodiment of the present invention.

FIG. 4A is a diagram showing a positional relation between the image-capturing unit 130 and the finger 99 according to the embodiment of the present invention. The image-capturing unit 130 includes an image pickup device 134 and the lens unit 133. The lens unit 133 is disposed between the image pickup device 134 and a subject (the finger 99). The distance between the lens unit 133 and the image pickup device 134 is the focal length f of the lens unit 133.

The distance between the lens unit 133 and the finger 99 is L. The distance L is made constant in the biological-information obtaining apparatus by fixing the positional relation between the insertion opening 123 and the image-capturing unit 130 according to the embodiment of the present invention.

The light coming from a base-side portion A of the finger 99 is refracted by the lens unit 133, and forms an image in an area C of the image pickup device 134. The light coming from a tip-side portion B of the finger 99 is refracted by the lens unit 133, and forms an image in an area D of the image pickup device 134. Thus, if a distance on the image pickup device 134 is Y, a distance X on the finger 99 is expressed by Eq. (1) given below.

$$X = Y \times L/f \qquad (1)$$

Here, it is assumed that the image pickup device 134 is divided into two regions, similarly to the case shown in FIG. 3. If the length of the image pickup device 134 along the extending direction of the finger 99 is K, the distance between the midpoint of the tip-side image portion and the midpoint of the base-side image portion is K/2, which is half the length of the image pickup device 134. If K/2 is substituted into the distance Y, the distance X on the finger 99 is expressed by Eq. (2) given below.

$$X = (K/2) \times L/f \qquad (2)$$

Thus, if the time difference T is obtained between the time when arteries are in an expanded state at the base-side portion A of the finger 99 and the time when arteries are in an expanded state at the tip-side portion B of the finger 99, a PWV P is calculated according to Eq. (3) given below.

$$P = X/T = \{(K/2) \times L/f\}/T \qquad (3)$$

Figure 4B:
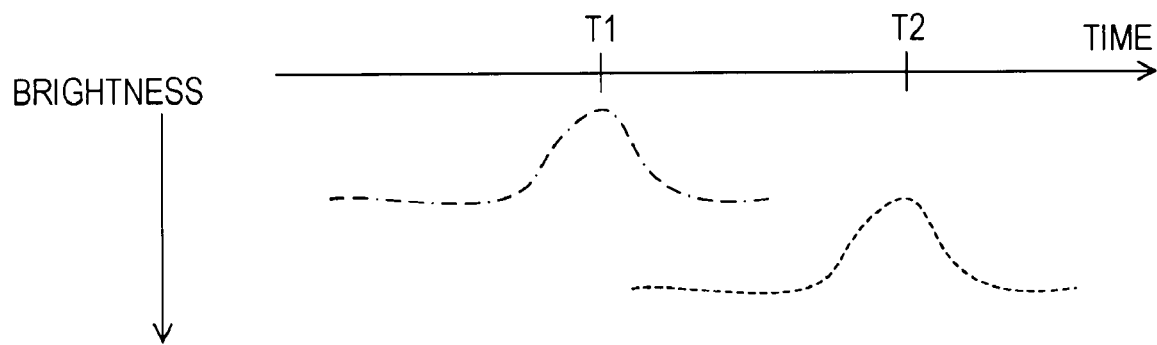

The brightness average of the image in the area C at the base-side portion A of the finger 99 becomes minimum at the time T1. This means the time T1 is when the arteries are in an expanded state at the base-side portion A. The brightness average of the image in the area D at the tip-side portion B of the finger 99 becomes minimum at the time T2. This means the time T2 is when the arteries are in an expanded state at the tip-side portion B. Thus, the value obtained by subtracting the time T1 from the time T2 represents the time difference T that was necessary for a pulse to move from the base-side portion A to the tip-side portion B. Here, brightness increases in the downward direction along the y-axis in the drawing shown in FIG. 4B.

Thus, the PWV P is calculated according to Eq. (4) given below.

$$P = \{(K/2) \times L/f\}/(T2-T1) \qquad (4)$$

Here, the focal length f is a value unique to the lens unit 133. The length K of the image pickup device 134 is a value unique to the image pickup device 134. Moreover, the distance L from the lens unit 133 to the finger 99 is constant in the biological-information obtaining apparatus. Thus, the focal length f, the length K, and the distance L can be stored in the parameter storing portion 246. Every time the time T1 and the time T2 are obtained, these fixed values are read from the parameter storing portion 246 and the PWV P is calculated according to Eq. (4) given above in the PWV calculation portion 247.

Figure 5:
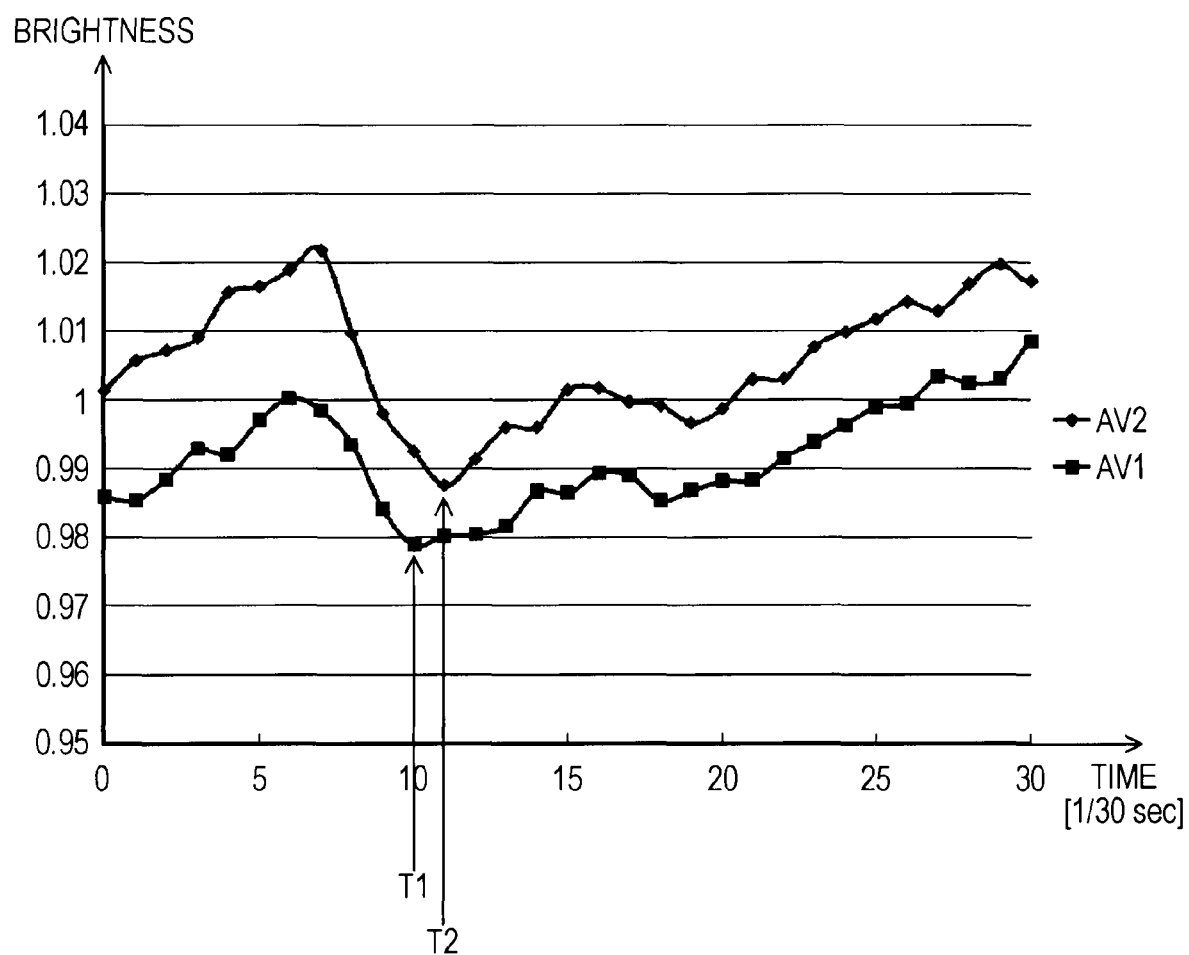
FIG. 5 is a diagram showing experimental data obtained from the biological-information obtaining apparatus according to the embodiment of the present invention.

FIG. 5 is a diagram showing experimental data obtained from the biological-information obtaining apparatus according to the embodiment of the present invention. In FIG. 5, the brightness averages $AV1(t)$ of the image portions concerning the base portion and the brightness averages $AV2(t)$ of the image portions concerning the tip portion are plotted at shooting intervals of 1/30 seconds.

The minimum brightness average $AV1(t)$ occurs at the tenth time T1, and the minimum brightness average $AV2(t)$ occurs at the eleventh time T2. Thus, it indicates that the travel time of a pulse is 1/30 seconds.

In current technology, if shooting intervals are approximately thirty images per second, such shooting intervals can be achieved even by home-use video cameras. It is expected that such shooting intervals will become shorter and the calculation accuracy of the PWV P will continue to improve with the further future development of large-scale integration (LSI) technology.

Next, an operation of the biological-information obtaining apparatus according to the embodiment of the present invention will be described with reference to the attached drawings.

Figure 6:
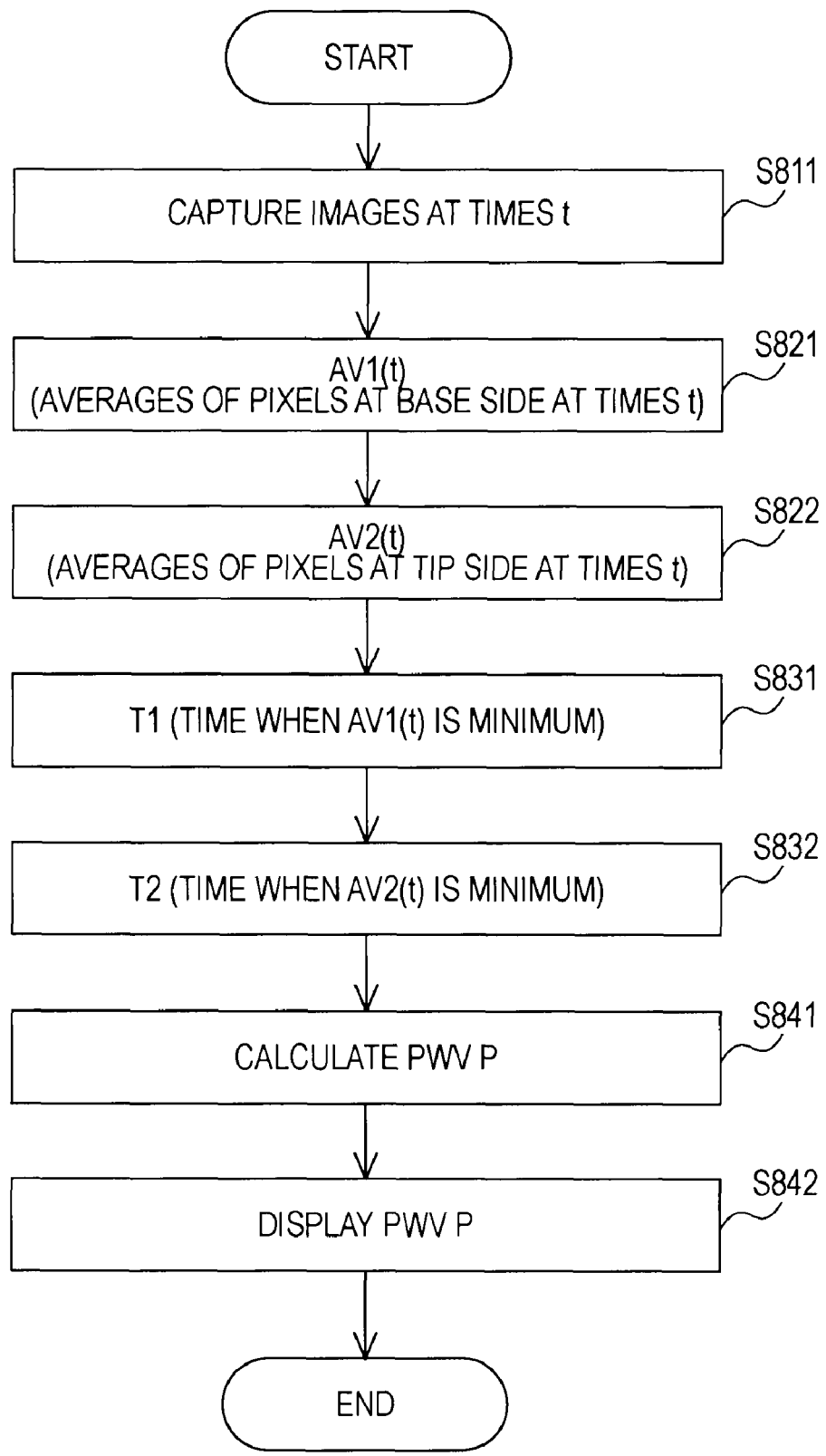
FIG. 6 is a flowchart showing an exemplary process of a biological information obtaining method according to the embodiment of the present invention.

FIG. 6 is a flowchart showing an exemplary process of a biological information (a PWV) obtaining method according to the embodiment of the present invention. In step S811, images captured by the image-capturing unit 130 at times t in time sequence are stored in the captured image storing portion 241.

In step S821, the base-side average calculation portion 242 calculates the brightness averages AV1(t) of the base-side image portions at the times t. In step S822, the tip-side average calculation portion 243 calculates the brightness averages AV2(t) of the tip-side image portions at the times t.

The base-side minimum-average time selecting portion 244 selects the time t at which the minimum brightness average AV1(t) is determined to occur in time sequence among the brightness averages AV1(t) calculated in step S821. The tip-side minimum-average time selecting portion 245 selects the time t at which the minimum brightness average AV2(t) is determined to occur in time sequence among the brightness averages AV2(t) calculated in step S822. That is, in step S831, the time t indicating the minimum brightness average AV1(t) is selected as T1. In step S832, the time t indicating the minimum brightness average AV2(t) is selected as T2.

In step S841, the PWV P is calculated in the PWV calculation portion 247 according to Eq. (1) on the basis of the times T1 and T2 selected in steps S831 and S832. In step S842, the calculated PWV P is displayed on the display 248.

According to the embodiments of the present invention, if one of the two regions is named as a first region and the other one of the two regions is named as a second region for each of the captured images, the base-side minimum-average time selecting portion 244 selects the time indicating the minimum brightness average with respect to the first regions of the images captured in time sequence, and the tip-side minimum-average time selecting portion 245 selects the time indicating the minimum brightness average with respect to the second regions of the images captured in time sequence. The PWV P can be calculated according to Eq. (1) on the basis of the time difference between the times.

The biological-information obtaining apparatus according to the embodiment of the present invention can be used as a vein authentication apparatus. That is, the use of such a vein authentication apparatus can achieve both identifying of an individual on the basis of vein authentication and obtaining of biological information (information regarding health) regarding the individual. For example, PWVs of a plurality of patients may be successively determined by using a single pulse oximeter in a short period of time in large hospitals. In this case, which determined PWV belonging to which patient is manually recorded in a medical certificate. Thus, the determined PWV may be linked to a wrong patient. However, if the biological-information obtaining apparatus according to the embodiment of the present invention is used, when the PWV is determined, which determined PWV belonging to which patient can be simultaneously specified by vein authentication. That is, a single apparatus can output "identified patient data" and "PWV data for the identified patient" as a pair of pieces of electronic data. The patient's electronic medical record is made using this pair of pieces of electronic data, and thus human error can be largely reduced.

As the embodiment of the present invention, an example of an achieved apparatus of transmissive type has been described above. Similarly to the case in which there are pulse oximeters of transmissive type and of reflective type, the apparatus according to the embodiment of the present invention is not limited to being an apparatus of transmissive type and may be an apparatus of reflective type. That is, a structure (of reflective type) in which a light-emitting unit and a light-receiving unit are disposed on the same side of a finger may be employed instead of the structure (of transmissive type) in which a light-emitting unit and a light-receiving unit are disposed on opposite sides of the finger.

In the embodiment of the present invention, although the minimum brightness average is used for the calculation, a maximum brightness average may be used instead, likewise.

The embodiment of the present invention is illustrated as an example of a way to realize the present invention. Although there is a correspondence between the embodiment and the features of the claims, which will be described below, the present invention is not limited thereto, and various modifications can be made without departing from the spirit and scope of the present invention.

That is, according to an embodiment of the present invention, light-emitting means corresponds to, for example, the light-emitting portion 122. An image sensor corresponds to, for example, the image pickup device 134. A lens corresponds to, for example, the lens unit 133. Extreme-occurrence-time obtaining means corresponds to, for example, the base-side minimum-average time selecting portion 244 and the tip-side minimum-average time selecting portion 245. Pulse-wave-velocity calculation means corresponds to, for example, the PWV calculation portion 247.

According to another embodiment of the present invention, light-emitting means corresponds to, for example, the light-emitting portion 122. An image sensor corresponds to, for example, the image pickup device 134. A lens corresponds to, for example, the lens unit 133. Parameter storing means corresponds to, for example, the parameter storing portion 246. Extreme-occurrence-time obtaining means corresponds to, for example, the base-side minimum-average time selecting portion 244 and the tip-side minimum-average time selecting portion 245. Pulse-wave-velocity calculation means corresponds to, for example, the PWV calculation portion 247.

According to another embodiment of the present invention, light-emitting means corresponds to, for example, the light-emitting portion 122. An image sensor corresponds to, for example, the image pickup device 134. A lens corresponds to, for example, the lens unit 133. Parameter storing means corresponds to, for example, the parameter storing portion 246. An extreme-occurrence-time obtaining process corresponds to, for example, steps S831 and S832. A pulse-wave-velocity calculation process corresponds to, for example, step S841.

The processes described in the embodiment of the present invention may be considered as a method having the series of processes or may be considered as a program for allowing a computer to execute the series of processes or as a recording medium having the program recorded thereon.

It should be understood by those skilled in the art that various modifications, combinations, sub-combinations and alterations may occur depending on design requirements and other factors insofar as they are within the scope of the appended claims or the equivalents thereof.

What is claimed is:

1. A biological-information obtaining apparatus comprising:
   light-emitting means for emitting light;
   an image sensor for capturing images, in time sequence, obtained by irradiating a living body with the light emitted and by causing the light to be transmitted through the living body;
   a lens for causing the images to be formed on the image sensor;
   extreme-occurrence-time obtaining means for obtaining a time T1 at which a first extreme value occurs in time sequence with respect to averaged brightness values of pixels in a first region in each of the captured images and a time T2 at which a second extreme value occurs in time sequence with respect to averaged brightness values of pixels in a second region in each of the captured images; and
   pulse wave velocity calculation means for calculating a pulse wave velocity P=(Y×L/f)/(T2−T1), where Y represents a distance on the image sensor, the distance corresponding to a distance between the first region and the second region, f represents a focal length of the lens, and L represents a distance between the lens and the living body when capturing the images.

2. The biological-information obtaining apparatus according to claim 1, wherein the light-emitting means emits monochromatic light.

3. The biological-information obtaining apparatus according to claim 1, wherein
   the extreme-occurrence-time obtaining means obtains the times T1 and T2 of the first region and the second region of each of the captured images based on halving the captured image, the time T1 being obtained for one of the first regions and the time T2 being obtained for one of the second regions, and
   the distance on the image sensor corresponds to a distance between midpoints of the first and second regions.

4. A biological-information obtaining apparatus comprising:
   light-emitting means for emitting light;
   an image sensor for capturing images, in time sequence, obtained by irradiating a living body with the light emitted and by causing the light to be transmitted through the living body;
   a lens for causing the images to be formed on the image sensor;
   parameter storing means for storing, as parameters, a length K of the image sensor, the focal length f of the lens, and a distance L between the lens and the living body when capturing images;
   extreme-occurrence-time obtaining means for obtaining a time T1 at which a first extreme value occurs in time sequence with respect to averaged brightness values of pixels in a first region in each of the captured images and a time T2 at which a second extreme value occurs in time sequence with respect to averaged brightness values of pixels in a second region in each of the captured images; and
   pulse wave velocity calculation means for calculating a pulse wave velocity P=((K/2)×L/f)/(T2−T1) on the basis of the times T1 and T2 obtained by the extreme-occurrence-time obtaining means and the parameters stored in the parameter storing means.

5. A method of obtaining biological information, the method being performed by a biological-information obtaining apparatus including light-emitting means for emitting light, an image sensor for capturing images, in time sequence, obtained by irradiating a living body with the light emitted and by causing the light to be transmitted through the living body, a lens for causing the images to be formed on the image sensor, and parameter storing means for storing, as parameters, a length K of the image sensor, the focal length f of the lens, and a distance L between the lens and the living body when capturing images, the method comprising the steps of:
   obtaining, by a hardware processor of the biological-information obtaining apparatus, a time T1 at which a first extreme value occurs in time sequence with respect to averaged brightness values of pixels in a first region in each of the captured images and a time T2 at which a second extreme value occurs in time sequence with respect to averaged brightness values of pixels in a second region in each of the captured images; and
   calculating, by the hardware processor of the biological-information obtaining apparatus, a pulse wave velocity P=((K/2)×L/f)/(T2−T1) on the basis of the times T1 and T2 and the parameters stored in the parameter storing means.

6. The method according to claim 5,
   wherein the first region corresponds to a base-side portion of a finger, and
   the second region corresponds to a tip-side portion of the finger.

7. A biological-information obtaining apparatus comprising:
   a light-emitting unit configured to emit light;
   an image sensor configured to capture images, in time sequence, obtained by irradiating a living body with the light emitted and by causing the light to be transmitted through the living body;
   a lens configured to cause the images to be formed on the image sensor;
   an extreme-occurrence-time obtaining unit configured to obtain a time T1 at which a first extreme value occurs in time sequence with respect to averaged brightness values of pixels in a first region in each of a plurality of captured images and a time T2 at which a second extreme value occurs in time sequence with respect to averaged brightness values of pixels in a second region in each of the plurality of captured images; and
   a pulse wave velocity calculation unit configured to calculate a pulse wave velocity P=(Y×L/f)/(T2−T1), where Y represents a distance on the image sensor, the distance corresponding to a distance between the first region and the second region, f represents the focal length of the lens, and L represents a distance between the lens and the living body when capturing the plurality of images.

8. A biological-information obtaining apparatus comprising:
   a light-emitting unit configured to emit light;
   an image sensor configured to capture images, in time sequence, obtained by irradiating a living body with the light emitted and by causing the light to be transmitted through the living body;
   a lens configured to cause the images to be formed on the image sensor;
   a parameter storage unit configured to store, as parameters, a length K of the image sensor, the focal length f of the lens, and a distance L between the lens and the living body when capturing the images;
   an extreme-occurrence-time obtaining unit configured to obtain a time T1 at which a first extreme value occurs in time sequence with respect to averaged brightness values of pixels in a first region, for each of the captured images and a time T2 at which a second extreme value occurs in time sequence with respect to averaged brightness values of pixels in a second region in each of the captured images; and a pulse wave velocity calculation unit configured to calculate a pulse wave velocity $P=((K/2) \times L/f)/(T2-T1)$ on the basis of the times T1 and T2 obtained by the extreme-occurrence-time obtaining unit and the parameters stored in the parameter storage unit.

* * * * *